(12) United States Patent
Song et al.

(10) Patent No.: US 12,092,623 B2
(45) Date of Patent: Sep. 17, 2024

(54) OPTICAL SENSOR FOR SENSING HYDROGEN GAS AND HYDROGEN GAS DETECTION SYSTEM INCLUDING THE SAME

(71) Applicant: KOREA INSTITUTE OF SCIENCE AND TECHNOLOGY, Seoul (KR)

(72) Inventors: Yong-Won Song, Seoul (KR); Sungjae Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 590 days.

(21) Appl. No.: 17/376,165

(22) Filed: Jul. 15, 2021

(65) Prior Publication Data
US 2022/0018821 A1   Jan. 20, 2022

(30) Foreign Application Priority Data
Jul. 15, 2020   (KR) .................. 10-2020-0087697

(51) Int. Cl.
*G01N 33/00*   (2006.01)
*G02B 6/12*   (2006.01)
*G02B 6/38*   (2006.01)

(52) U.S. Cl.
CPC ....... *G01N 33/005* (2013.01); *G02B 6/12004* (2013.01); *G02B 6/3845* (2013.01);
(Continued)

(58) Field of Classification Search
CPC .......... G01N 33/005; G02B 9/02; G02B 6/10; G02B 6/24; G01J 3/45
See application file for complete search history.

(56) References Cited

U.S. PATENT DOCUMENTS 5,392,117 A * 2/1995 Belleville ............ G02B 6/4215
                                                    250/227.27
5,783,152 A    7/1998 Nave
(Continued)

FOREIGN PATENT DOCUMENTS

KR   10-2006-0085027 A   7/2006
KR      10-0767535 B1   10/2007
(Continued)

OTHER PUBLICATIONS

D. Iannuzzi et al., "A fiber-top cantilever for hydrogen detection," Sensors and Actuators B, 2007, pp. 706-708, vol. 121, Elsevier B.V.
(Continued)

*Primary Examiner* — Abdullahi Nur
(74) *Attorney, Agent, or Firm* — CANTOR COLBURN LLP

(57) ABSTRACT

Embodiments relate to an optical sensor for sensing hydrogen gas, which includes an optical fiber through which light moves; a ferrule formed at one end of the optical fiber to surround the optical fiber; and a sensor module configured to form an interference wave according to a Fabry-Perot interferometer with respect to light that moves through the optical fiber, wherein the sensor module includes a sensing material that expands and contracts by reacting with hydrogen gas, and spectrum periodicity of the interference wave changes according to a volume change of the sensing material, and a hydrogen gas detection system including the optical sensor.

12 Claims, 14 Drawing Sheets

(52) U.S. Cl.
CPC .............. *G02B 2006/12121* (2013.01); *G02B 2006/12138* (2013.01); *G02B 2006/12159* (2013.01)

(56) References Cited

U.S. PATENT DOCUMENTS

| | | | |
|---|---|---|---|
| 6,921,894 B2* | 7/2005 | Swierkowski | G01P 15/093 250/227.21 |
| 7,286,237 B2 | 10/2007 | Grossman et al. | |
| 2003/0161580 A1* | 8/2003 | Morin | G02B 6/293 385/27 |
| 2008/0232745 A1* | 9/2008 | Knobloch | B23K 26/21 156/60 |
| 2009/0129721 A1* | 5/2009 | Chen | G01N 21/7703 385/12 |
| 2011/0170112 A1* | 7/2011 | Gibler | G01J 3/26 356/480 |
| 2013/0215429 A1* | 8/2013 | Song | G01N 21/7703 385/12 |
| 2013/0230271 A1 | 9/2013 | Lee et al. | |
| 2017/0049341 A1* | 2/2017 | Karabacak | A61B 5/02154 |
| 2019/0025122 A1* | 1/2019 | Nayak | G01J 3/26 |
| 2019/0391356 A1 | 12/2019 | Bae | |

FOREIGN PATENT DOCUMENTS

| | | |
|---|---|---|
| KR | 10-2008-0050864 A | 6/2008 |
| KR | 10-2013-0101390 A | 9/2013 |
| KR | 10-2018-0045931 A | 5/2018 |
| KR | 10-2019-0070716 A | 6/2019 |
| KR | 10-2020-0070682 A | 6/2020 |

OTHER PUBLICATIONS

Min Wang et al., "Fabry-Perot Interferometer Sensor Fabricated by Femtosecond Laser for Hydrogen Sensing," IEEE Photonics Technology Letters, 2013, pp. 713-716, vol. 25, No. 8.

Xinlei Zhou et al., "A compact hydrogen sensor based on the fiber-optic Fabry-Perot interferometer," Optics and Laser Technology, 2020, 6 pages, vol. 124, No. 105995.

Oleg Lupan et al., "Ultra-sensitive and selective hydrogen nanosensor with fast response at room temperature based on a single Pd/ZnO nanowire," Sensors and Actuators B: Chemical, 2018, pp. 1259-1270, vol. 254, Elsevier B.V.

Qi Liu et al., "Temperature dependent response/recovery characteristics of Pd/Ni thin film based hydrogen sensor," Sensors and Actuators B: Chemical, 2019, pp. 544-550, vol. 290, Elsevier B.V.

Ya-Nan Zhang et al., "Hydrogen sensor based on high-birefringence fiber loop mirror with sol-gel Pd/WO3 coating," Sensors and Actuators B: Chemical, 2017, pp. 71-76, vol. 248, Elsevier B.V.

J. I. Avila et al., "Optical properties of Pd thin films exposed to hydrogen studied by transmittance and reflectance spectroscopy," Journal of Applied Physics, 2010, vol. 107, No. 023504, American Institute of Physics.

Noah J. J. Johnson et al., "Facets and vertices regulate hydrogen uptake and release in palladium nanocrystals," Nature Materials, 2019, pp. 454-458, vol. 18.

Jixiang Dai et al., "Optical hydrogen sensor based on etched fiber Bragg grating sputtered with Pd/Ag composite film," Optical Fiber Technology, 2013, pp. 26-30, vol. 19, Elsevier Inc.

\* cited by examiner

OPTICAL SENSOR FOR SENSING HYDROGEN GAS AND HYDROGEN GAS DETECTION SYSTEM INCLUDING THE SAME

CROSS-REFERENCE TO RELATED APPLICATION

This application claims priority to Korean Patent Application No. 10-2020-0087697, filed on Jul. 15, 2020, and all the benefits accruing therefrom under 35 U.S.C. § 119, the contents of which in its entirety are herein incorporated by reference.

TECHNICAL FIELD

Embodiments relate to a sensor for sensing hydrogen gas, and more particularly, to an optical sensor for detecting hydrogen by using a change in a pattern of an interference wave spectrum generated by a reaction between a sensor module and hydrogen.

NATIONAL RESEARCH AND DEVELOPMENT SUPPORT

This work was supported by the Basic Science Research Program (Grant No. 2019R1A2C2087693) of the National Research Foundation (NRF) funded by the Ministry of Science and ICT, Republic of Korea.

BACKGROUND ART

Hydrogen gas ($H_2$) is widely used in petroleum, chemical and aerospace industries. Hydrogen gas ($H_2$) has a high risk due to a high diffusion coefficient (0.16 $cm^2/s$ in air), low ignition energy (0.02 mJ), high combustion heat (285.8 kJ/mol) and a high explosive concentration range (4-75%). Since hydrogen gas ($H_2$) has colorless, odorless and tasteless properties, the hydrogen gas cannot be detected by human senses, so there is a rising interest in technology to quickly detect hydrogen gas ($H_2$) with high sensitivity, high accuracy and high selectivity.

In the prior art, an electrically operated hydrogen sensor was used. However, the electric hydrogen sensor has a limitation in that an electric spark may occur at or around the sensor, which gives a risk of explosion.

DISCLOSURE

Technical Problem

According to one aspect of the present disclosure, it is possible to provide an optical sensor configured such that a wavelength of an interference wave formed by a fiber Fabry-Perot interferometer changes when a sensor module reacts with hydrogen, in order to detect hydrogen gas by using a change in the pattern of a spectrum of the interference wave.

In addition to the optical sensor, it is possible to provide a hydrogen gas detection system for detecting a concentration of hydrogen gas based on a change in the pattern of a spectrum of interfering light of the optical sensor.

Technical Solution

An optical sensor for sensing hydrogen gas according to an aspect of the present disclosure may comprise an optical fiber through which light moves; a ferrule formed at one end of the optical fiber to surround the optical fiber, and a sensor module configured to form an interference wave according to a Fabry-Perot interferometer with respect to light that moves through the optical fiber and is output from the optical fiber. The sensor module includes a sensing material that expands and contracts by reacting with hydrogen gas, and spectrum periodicity of the interference wave changes according to a volume change of the sensing material.

In an embodiment, the sensor module may include a module case having a sidewall for forming a cavity so that one end of the sidewall is in contact with the ferrule; a support layer provided in contact with the other end of the sidewall; and a hydrogen reaction layer formed on the support layer and made of the sensing material. The light output from the optical fiber may move through the cavity between the ferrule and the support layer.

In an embodiment, the interference wave may be formed by repeated reflection and transmission of light between a first reflection surface formed between the cavity and the optical fiber and a second reflection surface formed between the cavity and the support layer. Here, the spectrum periodicity of the interference wave may change as the support layer is deformed according to a volume change of the hydrogen reaction layer to change a distance between the second reflection surface and the first reflection surface.

In an embodiment, the optical sensor may further comprise a holder configured to fix a contact portion of the module case and the ferrule.

In an embodiment, one end of the ferrule may be inserted into a perforated hole of the module case so that the sensor module and the ferrule come into contact.

In an embodiment, the sensing material may include palladium (Pd).

In an embodiment, one ends of the ferrule and the optical fiber toward the cavity may be polished perpendicular to the direction in which the light is output from the optical fiber.

A hydrogen gas detection system according to another aspect of the present disclosure may comprise an optical sensor according to the former embodiments; a light source configured to irradiate light to the optical fiber of the optical sensor; and an optical spectrum analyzer configured to detect whether hydrogen gas is present or to measure a concentration of the hydrogen gas based on the change of spectrum periodicity of the interference wave formed at the optical sensor.

In an embodiment, the hydrogen gas detection system may further comprise a circulator having first to third ports and configured to output the light formed at the light source and input to the first port to the sensor module connected to the second port, and to output the interference wave formed at the sensor module and input to the second port to the optical spectrum analyzer connected to the third port.

Advantageous Effects

Since the hydrogen gas detection system according to one aspect of the present disclosure detects hydrogen gas by using an optical sensor, there is no fear of an electric spark, and thus there is no risk of explosion. Such an optical sensor has the same level of sensitivity, accuracy, selectivity and detection speed as a conventional electronic device-based sensor.

In addition, the optical sensor may detect hydrogen gas without any influence of the surrounding environment, such as surrounding gas or liquid.

In addition, if the optical sensor is used as a sensor node in a system, a power source or data communication material of the node itself is not required, so the system configuration is simple and economical.

In addition, the hydrogen gas detection system may operate a plurality of remote sensors and a single analysis device (OSA, Optical Spectrum Analyzer).

BEST MODE

It should be noted that the technical terms used in this specification are only used to describe specific embodiments, and are not intended to limit the present disclosure. In addition, the technical terms used in this specification should be interpreted as the meaning generally understood by those skilled in the art, unless otherwise defined in this specification, and should not be construed in an excessively inclusive meaning or in an excessively narrowed meaning. In addition, when any technical term used in this specification is an incorrect technical term that does not accurately express the idea of the technology disclosed in this specification, it should be understood by being replaced with a technical term that can be correctly understood by those skilled in the art.

Also, the singular expression used in this specification includes the multiple expressions, unless clearly indicated otherwise in the context. In this specification, the terms such as "comprise" or "include" should not be construed as necessarily including all of several components or steps described in the specification, and they should be construed as being capable of not including some components or some steps or further including additional components or steps.

In addition, the suffix "unit" used for the terms of components in this specification is endowed or used in consideration of ease in writing the specification, and does not have a meaning or role distinct from each other by itself.

In addition, in describing the technology disclosed in this specification, if it is determined that a detailed description of a related known technology may obscure the gist of the technology disclosed in this specification, the detailed description thereof will be omitted. In addition, it should be noted that the accompanying drawings are only for easy understanding of the idea of the technology disclosed in this specification, and the idea of the technology should not be limited by the accompanying drawings.

Hereinafter, embodiments disclosed in this specification will be described in detail with reference to the accompanying drawings.

Figure 1A:
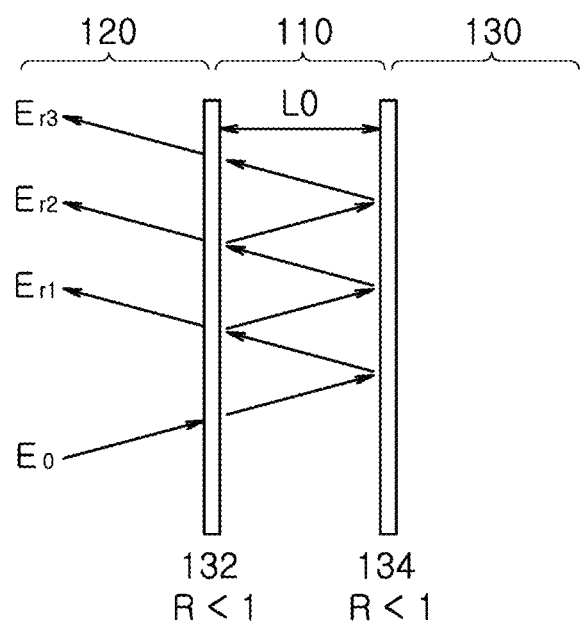
FIGS. 1A to 1C are diagrams for explaining the principle of a fiber Fabry-Perot interferometer.
Figure 1B:
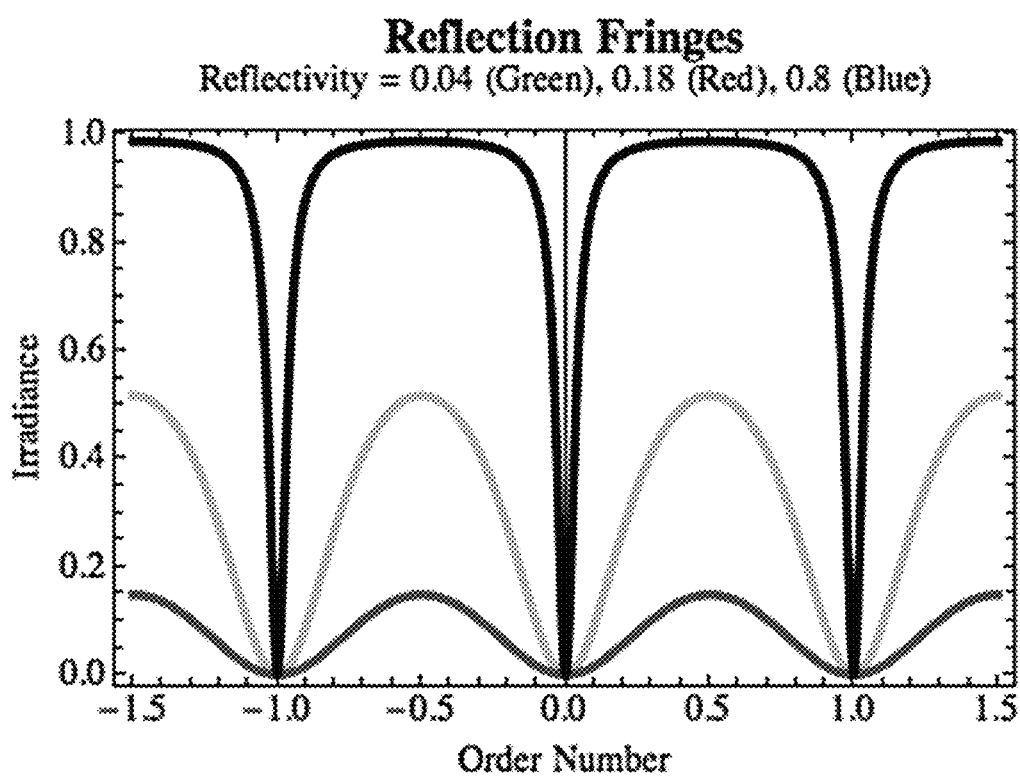
Figure 1C:
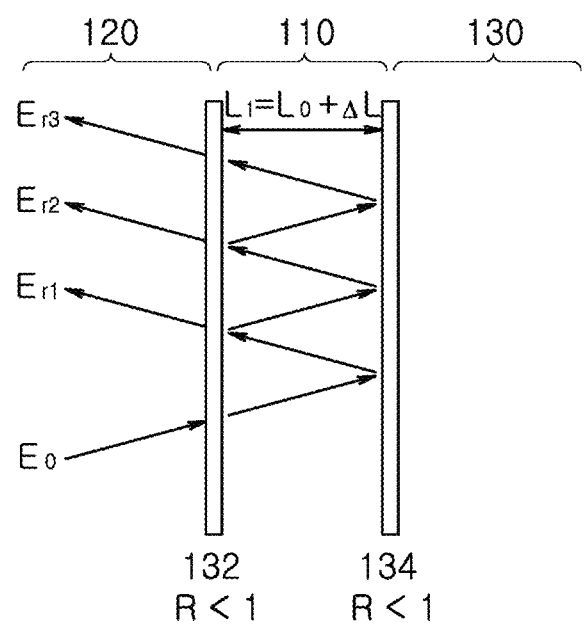

FIGS. 1A to 1C are diagrams for explaining the principle of a fiber Fabry-Perot interferometer.

The fiber Fabry-Perot interferometer (FFPI) has periodicity in the spectrum of an interference wave reflected from two reflective surfaces. Here, if a distance between the two surfaces or a refractive index of the material of the interferometer changes, the periodicity also changes. The fiber Fabry-Perot interferometer uses the principle of analyzing a spectrum by using the change in periodicity. This will be described in detail as follows.

FIG. 1A shows a case where two reflective surfaces 132, 134 have a distance L0 and the space between the surfaces is filled with a material having a refractive index n0.

The two surfaces 132, 134 include a first surface 132 serving as a boundary for the material between a region 120 and the two surfaces 132, 134, and a second surface 134 serving as a boundary of an inner region 110 and an outer region 130 between the surfaces 132, 134. The first surface 132 and the second surface 134 have reflectivity (R) less than 1.

Light E0 having an arbitrary wavelength ($\lambda$) moves in the region 120 connected to one surface of the first surface 132 and is irradiated to the first surface 132. The light passing through the first surface 132 is incident on the region 110 between the first surface 132 and the second surface 134.

The light incident on the region 110 moves again to the second surface 134. Due to the difference in refractive index for the regions 110, 120, 130 and/or the reflectivity of the surfaces 132, 134, the light moving in the above movement path is partially or entirely reflected on the first surface 132 and the second surface 134. Depending on the characteristics of the second surface 134, some of the moved light may be transmitted to the outside. The reflected light passes through the first surface 132 and moves again to the region 120.

Accordingly, the light repeatedly reflected and transmitted between the two surfaces 132, 134 forms a plurality of reflected waves (Er1, Er2, Er3 . . . ) returning to the region 120 again. The plurality of reflected waves (Er1, Er2, Er3) interfere with each other within the region 120, and form an interference wave finally determined due to the interference.

FIG. 1B is a diagram showing the spectrum of the interference wave of FIG. 1A.

The interference wave has a constant wavelength, and the spectrum of the interference wave shows periodicity depending on the wavelength. The periodicity is expressed as a function of the refractive index and the distance between the two surfaces 132, 134.

As shown in FIG. 1B, the spectrum of the interference wave has the same peak position regardless of the components included in the incident light. Specifically, the position of the peak does not change depending on the wavelength (component) of the incident light, but a difference in transmittance and reflectivity at the boundary of the reflection surface occurs, so the intensity of the peak may change.

Using the change in spectrum periodicity of the final interference wave formed in this way for the purpose of detecting a material is called a fiber Fabry-Perot interferometer (FFPI).

If one reflective surface reacts with a specific external material so that the reflective surface is deformed to change the distance (L) of the interferometer, the periodic pattern of the spectrum may be changed.

As a result, the FFPI may detect an external influence that causes the material change of the FFPI, by means of the change in spectrum periodicity of the interference wave.

FIG. 1C shows a case where the distance (L) between two surfaces 132, 134 changes from L0 to L1 as the distance between two surfaces 132, 134 increases by ΔL.

If the distance between the two surfaces 132, 134 is changed, the number of final stationary waves formed by reflection of the incident wave increases as the resonance length increases, so the spectrum period of the interference wave is also shortened. Therefore, on the spectrum, it is possible to observe a phenomenon that the shapes of mountains and valleys of the observed spectrum shifts to one side.

If at least a portion of any one of the two surfaces 132, 134 is deformed so that the distance between the two surfaces 132, 134 increases, the wavelength variance (Δλ) according to the periodic change of the interference wave with respect to the wavelength (λ) of the incident wave is expressed as Equation 1 below.

$$\Delta\lambda = \frac{\lambda(n_0 \Delta L)}{n_0 L_0}$$ [Equation 1]

Here, Δλ represents a wavelength variance of the interference wave with respect to the wavelength of the incident wave, λ represents a wavelength of the incident wave, n0 represents a refractive index of the material between the two surfaces, ΔL represents a distance variance between the two surfaces, and L0 represents an initial distance between the two surfaces.

As described above, the fiber Fabry-Perot interferometer may detect an external influence that causes a change in the distance of the material 110 filled between the two surfaces 132, 134, based on the wavelength variance (ΛΛ) of the interference wave according to the change in distance between any two surfaces 132, 134 and the resultant change in spectrum periodicity.

Hereinafter, a gas detection device using the principle of the fiber Fabry-Perot interferometer will be described.

Figure 2:
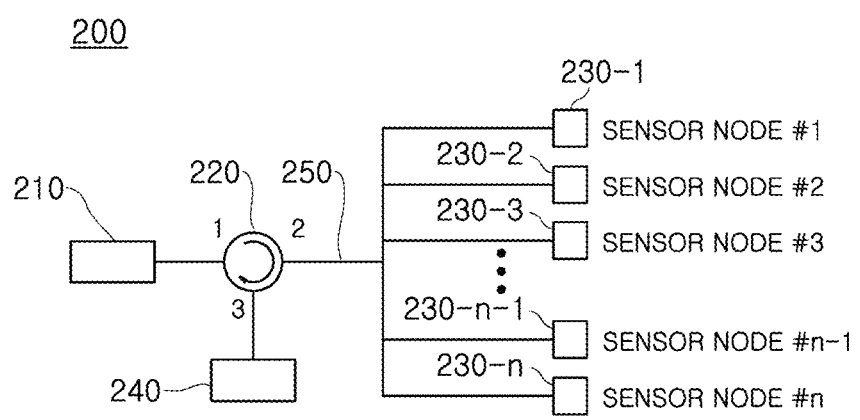
FIG. 2 is a schematic diagram showing a hydrogen gas detection system, according to an embodiment of the present disclosure.

FIG. 2 is a schematic diagram showing a hydrogen gas detection system, according to an embodiment of the present disclosure.

Referring to FIG. 2, the hydrogen gas detection system 200 may include a light source 210, a circulator 220, a sensor module 230, an optical analyzer 240, and an optical fiber 250. The optical sensor includes at least a portion of the sensor module 230 and the optical fiber 250.

In certain embodiments, the hydrogen gas detection system 200 may include a plurality of sensor modules 230 and a plurality of optical fibers 250. For example, as shown in FIG. 2, the hydrogen gas detection system 200 may include an n number of sensor modules 230 and an n number of optical fibers 250.

The light source 210 may generate white light, broadband light or laser light. The light generated from the light source 210 may be irradiated to an input port of the circulator 220. Also, the light may be irradiated to the sensor module 230 through the circulator 220.

The light source 210 may be a laser diode or a broadband light source.

In an embodiment, the light source 210 may be an Er-doped fiber amplifier (EDFA) to generate the broadband light.

The circulator 220 may include first to third ports. The circulator 220 may be configured to output light input to the first port to the second port and to output light input to the second port to the third port.

In an embodiment, the circulator 220 may output the light formed at the light source 210 and input to the first port to the sensor module 230 connected to the second port, and output the interference wave formed at the sensor module 230 and input to the second port to the optical analyzer 240 connected to the third port. In certain embodiments, the light input to the second port is branched to correspond to the number of sensor modules 230 in the system.

That is, the circulator 220 may be positioned between the light source 210, the sensor module 230 and the optical analyzer 240 to switch the path of light generated from the light source 210. At this time, the first port of the circulator 220 may be connected to the light source 210, the second port may be connected to the sensor module 230, and the third port may be connected to the optical analyzer 240.

The circulator 220 may include a mirror or a polarization control element that reflects the light to adjust the path of the light.

The sensor module 230 forms an interference wave by the principle of the fiber Fabry-Perot interferometer. The sensor module 230 may form the interference wave according to the principle of the fiber Fabry-Perot interferometer with respect to the light irradiated from the light source 210.

The sensor module 230 is configured to form a first reflection surface and a second reflection surface that act as two surfaces of the fiber Fabry-Perot interferometer to form the interference wave. The light passing through the optical fiber 250 is incident on the first reflection surface and moves toward the second reflection surface. At least a portion of the light moving toward the second reflection surface is reflected and passes through the first reflection surface again. The light moving in this way may form an interference wave having an arbitrary wavelength and spectrum periodicity by repeated reflection and transmission between two surfaces.

In an embodiment, the sensor module 230 includes a sensing material that expands or contracts by reacting with hydrogen gas. For example, the sensing material may be a material that expands by adsorption with hydrogen gas or contracts when it does not combine with the hydrogen gas.

In an embodiment, the sensing material may also include palladium (Pd).

The sensing material is formed to contact the second reflection surface. Due to this, the volume change of the sensing material causes deformation of the second reflection surface. Due to the deformation of the second reflection surface, the distance between the first reflection surface and the second reflection surface where light moves changes, so the wavelength of the interference wave may change.

The sensor module 230 will be described in more detail below with reference to FIG. 3 and the like.

The optical analyzer 240 detects whether hydrogen gas is present and/or measures a hydrogen gas concentration based on the wavelength change of the interference wave. That is, the optical analyzer 240 observes the spectrum of the interference wave formed in the sensor module 230, and determines whether the hydrogen gas is present and/or calculates the hydrogen gas concentration based on whether the spectrum periodicity changes.

To this end, the optical analyzer 240 may measure the spectrum of the interference wave. The optical analyzer 240 may display the spectrum of the interference wave incident to the optical analyzer 240 on a display. The characteristics of the light by the optical analyzer 240 may include wavelength, periodicity, light intensity, or the like.

In an embodiment, the optical analyzer 240 may be an optical spectrum analyzer (OSA). The OSA 240 is used to detect the spectrum of the interference wave in the broadband light. Each component of the hydrogen gas detection system 200 may be connected through the optical fiber 250. Alternatively, each component may be connected through a planar optical waveguide instead of the optical fiber 250.

The optical fiber 250 may provide a movement path of light formed by the light source 210 using total reflection. The optical fiber 250 may connect components of the hydrogen sensing system 200 and provide a movement path for light formed by the light source 210 to move between the components.

Specifically, in the optical fiber 250, the light formed at the light source 210 is irradiated to the sensor module 230 through the circulator 220, and the interference wave formed at the sensor module 230 may be irradiated to the optical analyzer 240 through the circulator 220.

The optical fiber 250 may provide a movement path of light formed by the light source 210 using total reflection. That is, the optical fiber 250 may provide a movement path to irradiate the light generated at the light source 210 to the sensor module 230.

The optical fiber 250 irradiates light to the sensor module 230 without loss of energy. The optical fiber 250 may include a core and a cladding that induce total reflection of light.

In other embodiments, the movement path of light formed by the light source 210 may be provided by using a planar optical waveguide instead of the optical fiber 250. The optical waveguide has a shorter length and a much greater thickness compared to the optical fiber 250, which enables intensive configuration of the sensor module 230 and the hydrogen gas detection system 200 including the sensor module 230 and may be useful in changing the diameter of light formed at the light source 210.

Not all of the components of the hydrogen gas detection system shown in FIG. 2 are essential, and the hydrogen gas detection system 200 may be implemented with more or fewer components than those shown in FIG. 2.

Figure 3:
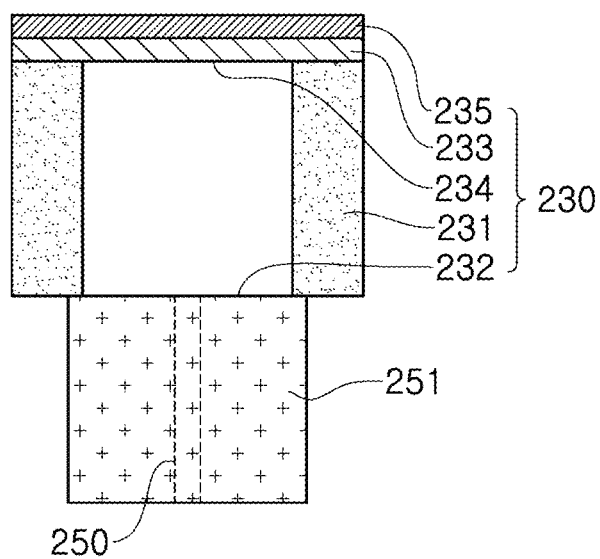
FIG. 3 is a schematic diagram of an optical sensor, according to an embodiment of the present disclosure.

FIG. 3 is a schematic diagram of an optical sensor, according to an embodiment of the present disclosure.

Referring to FIG. 3, the optical sensor may also include a sensor module 230 and an optical fiber 250. The sensor module 230 is coupled to one end of the optical fiber 250 to receive light from the optical fiber 250.

The optical fiber 250 may be supported by a ferrule 251. The ferrule 251 may be formed at one end of the optical fiber 250. The optical fiber 250 may be inserted into the ferrule 251 to form one assembly (hereinafter, referred to as an optical fiber ferrule assembly).

The ferrule 251 may be formed to surround the optical fiber 250. The ferrule 251 has a perforated hole. One end of the optical fiber 250 is inserted into the perforated hole of the ferrule 251.

Due to this, the ferrule 251 blocks a gas or fluid outside the sensor module 230 from entering the sensor module 230. As a result, it is prevented that an external gas or fluid changes the distance between the first reflection surface 232 and the second reflection surface 234 formed inside the sensor module 230.

The ferrule 251 functions to fix the optical fiber 250 to the sensor module 230. The cross section of the ferrule 251 corresponds to the bottom surface of the sensor module 230 therebelow or is configured to be inserted therein. In some embodiments, the cross section of ferrule 251 may have a diameter of 1 mm to 3 mm, in particular approximately 2 mm.

As the optical fiber 250 is supported by the ferrule 251, light is irradiated perpendicular to the sensor module 230. The ferrule 251 may be made of, for example, ceramic, but is not limited thereto.

The sensor module 230 may form an interference wave based on the principle of the fiber Fabry-Perot interferometer with respect to the light formed from the light source 210 and received through the optical fiber 250.

The sensor module 230 is configured to be detachable from and attachable to the optical fiber ferrule assembly.

In an embodiment, the sensor module 230 may include a module case 231, a support layer 233 and a hydrogen reaction layer 235.

The module case 231 is configured such that the light of the optical fiber 250 moves to the hydrogen reaction layer 235 in a state where the sensor module 230 is combined with the optical fiber ferrule assembly.

The module case 231 may have a perforated hole. The module case 231 includes a sidewall to form a cavity. The bottom surface of module case 231 is in contact with the optical fiber ferrule assembly. One end of the sidewall is in contact with the ferrule 251.

Due to this contact structure, the first reflection surface 232 of the interferometer is formed on the bottom surface of the module case 231.

The first reflection surface and the second reflection surface of the interferometer in the sensor module 230 form a cavity. In an embodiment, the inside of the perforated hole may be filled with air.

The module case 231 attached to the optical fiber ferrule assembly has a sealed structure so that the light output from the optical fiber 250 is not exposed to the fluid or gas outside the sensor module 230. The module case 231 shown in FIG. 3 is only for explaining the cavity therein, and does not mean that the actual module case 231 is opened to the outside.

The support layer 233 is disposed on the upper surface of the module case 231. The support layer 233 is in contact with the other end of the sidewall of the module case 231, namely a top of the sidewall, which is opposite to one end of the sidewall in contact with the ferrule 251.

Due to this arrangement, the second reflection surface 234 of the interferometer is formed on the bottom surface of the support layer 233. The support layer 233 is configured to come into contact with the hydrogen reaction layer 235 and be deformed according to the volume change of the hydrogen reaction layer 235.

To this end, the support layer 233 is made of a deformable material. The support layer 233 may be made of a material including, for example, any one selected from the group consisting of $Si_3N_4$, $SiO_2$, $Al_2O_3$, and the like, or a combination thereof.

In addition, the support layer 233 may be formed to have a thickness of several μm or less, for example 2 μm or less or 1 μm or less.

The hydrogen reaction layer 235 is formed on the support layer 233. The hydrogen reaction layer 235 is configured to change its volume by reacting with hydrogen gas around the sensor module 230. The hydrogen reaction layer 235 is made of a sensing material that expands easily in volume by reacting with hydrogen gas. As described above, the sensing material may include palladium (Pd).

The sensor module 230 has a structure that is easily attachable to and detachable from the optical fiber ferrule assembly. In addition, the sensor module 230 is configured to maintain coupling when being coupled to the optical fiber ferrule assembly.

Figure 4A:
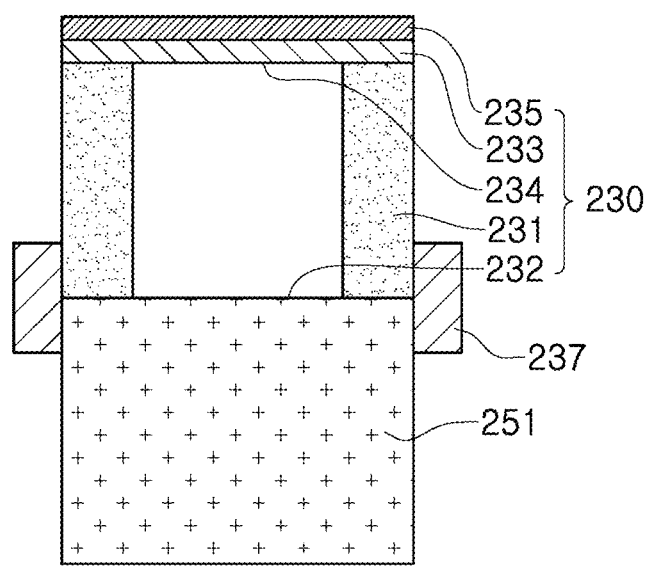
FIGS. 4A and 4B are sectional views showing an optical sensor of the first type, according to an embodiment of the present disclosure.
Figure 4B:
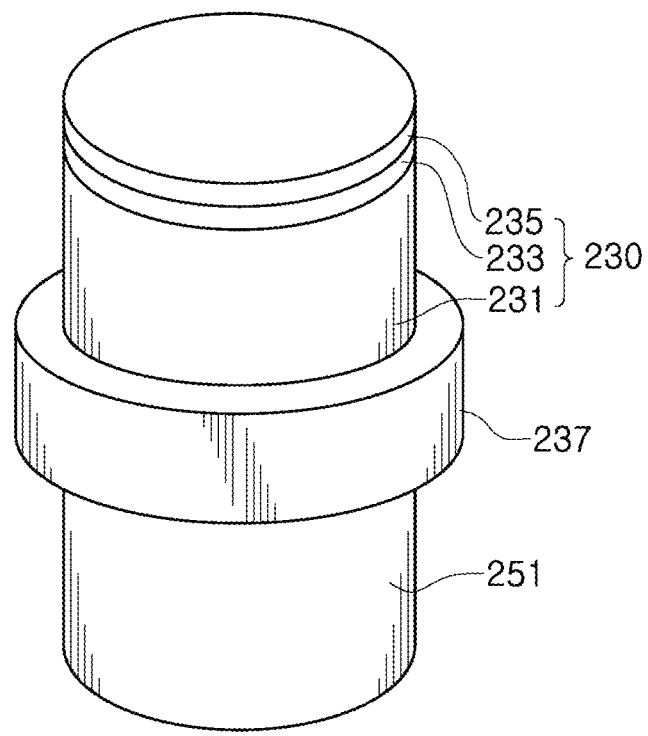

FIGS. 4A and 4B are sectional views showing an optical sensor of the first type, according to an embodiment of the present disclosure.

Referring to FIGS. 4A and 4B, the optical sensor may further include a holder 237. The inner surface of the holder 237 is fixed in contact with the outer surface of the module case 231 and the outer surface of the optical fiber ferrule assembly at the same time. In the optical sensor, the holder 237 fixes the contact state between the optical fiber ferrule assembly and the module case 231, so that the distance between the surfaces does not change unless the hydrogen reaction layer 235 deforms by reacting with hydrogen gas.

The holder 237 may also be configured to be easily separated such that the sensor module 230 is easily detachable from the optical fiber ferrule assembly.

In an embodiment, the inner diameter of the holder 237 may be configured to correspond to the outer diameter of the module case 231 and the outer diameter of the optical fiber ferrule assembly. For example, as shown in FIGS. 4A and 4B, the module case 231 and the optical fiber ferrule assembly are manufactured to have the same outer diameter, and the holder 237 aligns and fixes them.

Figure 5:
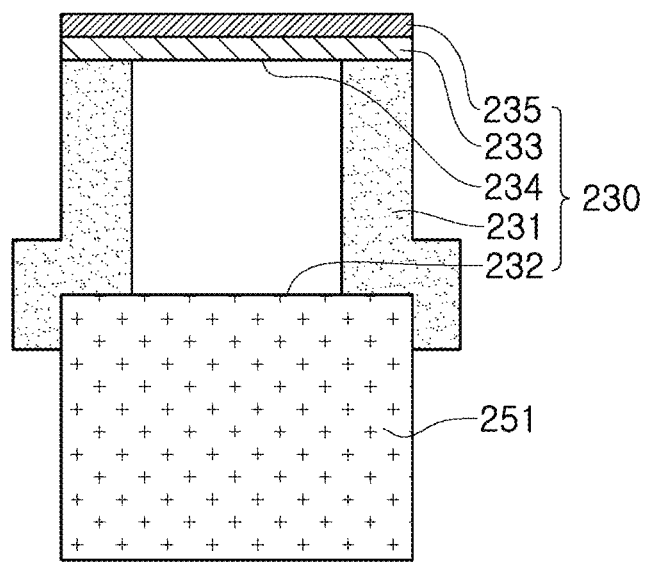
FIG. 5 is a diagram showing an optical sensor of the second type, according to another embodiment of the present disclosure.

FIG. 5 is a diagram showing an optical sensor of the second type, according to another embodiment of the present disclosure.

Referring to FIG. 5, the module case 231 is configured such that one end of the optical fiber ferrule assembly is inserted into the perforated hole. In the second type of the optical sensor, the sensor module 230 and the optical fiber ferrule assembly are combined due to the inner structure of the module case 231.

The sensor module 230 of FIGS. 3 to 5 may form an interference wave according to the principle of the fiber Fabry-Perot interferometer with respect to the light formed from the light source 210 and incident through the optical fiber 250.

In the sensor module 230, the bottom surface of the module case 231 serves as the first reflection surface of the interferometer. The bottom surface of the support layer 233 is in contact with the upper surface of the module case 231 and serves as the second reflection surface of the interferometer. Periodic constructive interference occurs due to repeated reflection and transmission of light between the bottom surface of the module case 231 and the bottom surface of the support layer 233 to form a plurality of stationary waves between the two reflection surfaces, thereby forming a final interference wave with periodicity on the spectrum. The interference wave formed through the fiber Fabry-Perot interferometer including the reflection surfaces 232, 234 may have an arbitrary wavelength depending on the distance between the two surfaces 232, 234.

Since the cavity between the two surfaces 232, 234 is blocked from the outside by the module case 231, the refractive index of the material filling the cavity acts as a constant. Therefore, the interference wave formed through the interferometer may have an arbitrary wavelength depending on the distance between the two surfaces 232, 234.

The optical sensor including the sensor module 230 detects hydrogen gas based on the change of the interference wave.

Figure 6:
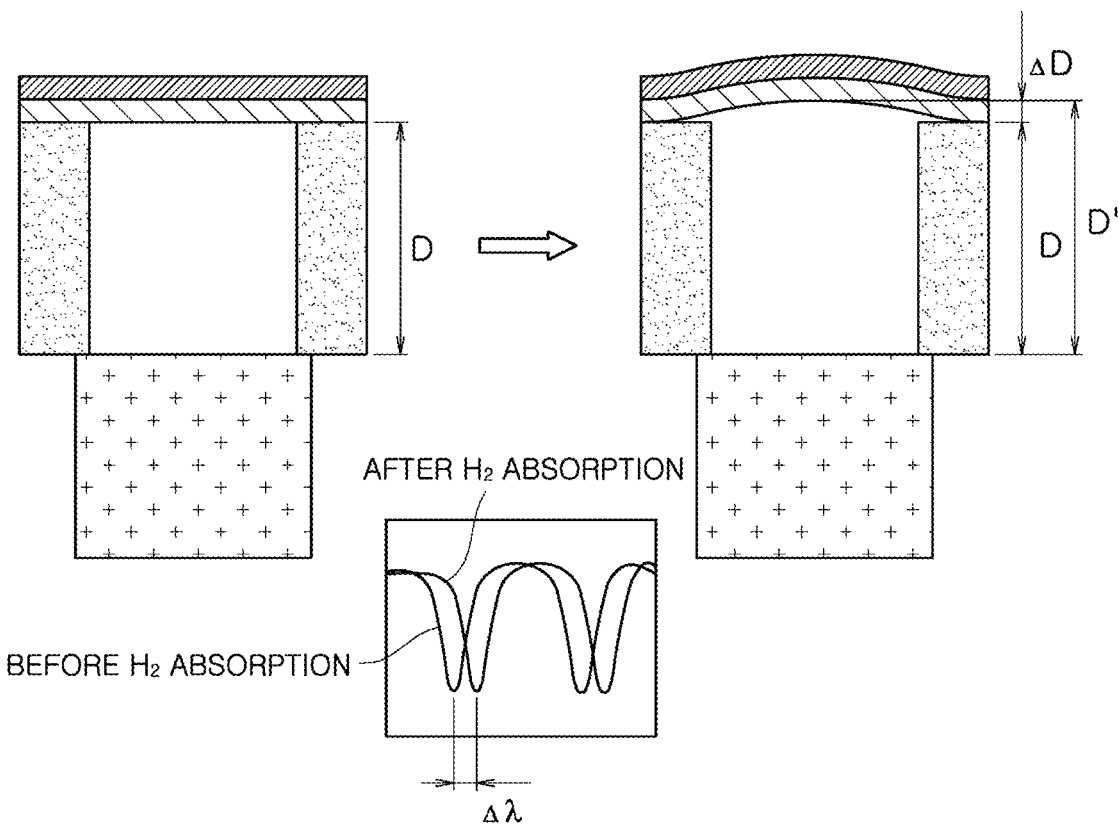
FIG. 6 is a conceptual diagram for explaining an operation principle of the optical sensor of FIG. 3.

FIG. 6 is a conceptual diagram for explaining an operation principle of the optical sensor of FIG. 3.

In the hydrogen gas detection system 200, light is irradiated to the sensor module 230. The hydrogen gas detection system 200 may generate light using the light source 210.

In some embodiments, the hydrogen gas detection system 200 may further include the EDFA, and the amplified light may be irradiated to the sensor module 230.

An interference wave is formed by the irradiated light. By the sensor module 230, it is possible to form an interference wave according to the principle of the fiber Fabry-Perot interferometer with respect to the light incident from the light source 210.

The hydrogen reaction layer 235 made of a sensing material may expand or contract by hydrogen gas. In the absence of external hydrogen gas, the volume of the sensing material of the hydrogen reaction layer 235 does not change. Therefore, the distance (D) of the cavity formed by the first surface 232 and the second surface 234 does not change.

Meanwhile, if the sensing material of the hydrogen reaction layer 235 expands by combining with the external hydrogen gas, the stacked structure composed of the hydrogen reaction layer 235 and the support layer 233 is deformed. Due to this deformation, the distance between the two surfaces 232, 234 changes. For example, if the sensing material absorbs hydrogen gas, as shown in FIG. 6, the distance of between the two surfaces 232, 234 increases from D to D' (=D+$\Delta$D), and as a result, the periodicity of the spectrum of the interference wave of the fiber Fabry-Perot interferometer may change. The periodicity change of the spectrum of the interference wave may be expressed as a position shift of the peak of the spectrum of the interference wave.

The optical sensor may also be used to detect hydrogen according to whether the spectrum period of the interference wave changes.

The hydrogen gas detection system 200 obtains the interference wave output from the optical sensor by using the optical analyzer 240. The obtained interference wave may be an interference wave whose wavelength is changed so that the period of the spectrum is changed. If the spectrum period is changed according to the analysis result, the optical analyzer 240 may output the presence or absence of the hydrogen gas and/or the concentration of the detected hydrogen gas.

For example, if the wavelength changes compared to when the hydrogen gas is not present, the hydrogen gas detection system 200 may determine that the hydrogen gas is present in the air.

In addition, the hydrogen gas detection system 200 may measure the concentration of hydrogen gas based on the degree of wavelength change. In FIG. 6, the degree of change in the periodicity of the spectrum of interference wave corresponds to $\Delta$D.

Figure 7:
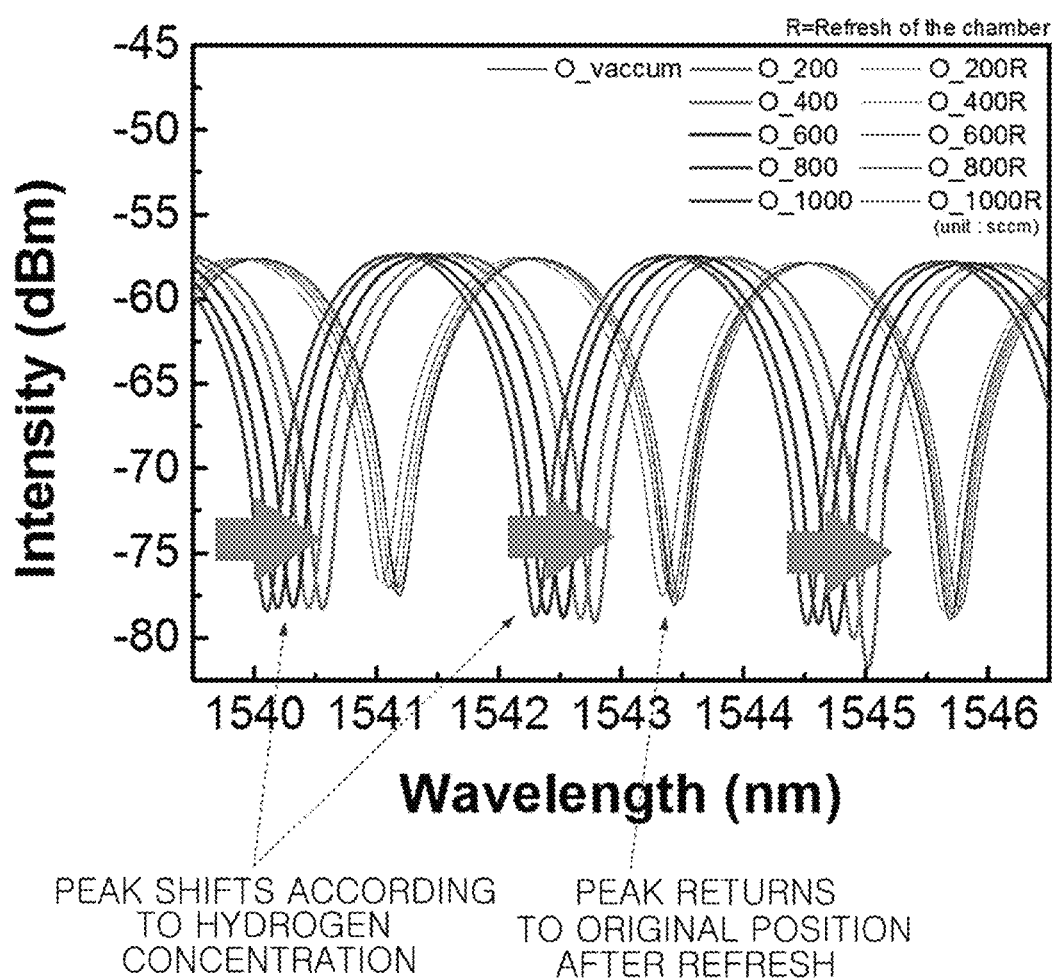
FIG. 7 is a graph showing the shift of a wavelength spectrum according to a hydrogen concentration, according to an embodiment of the present disclosure.
Figure 8:
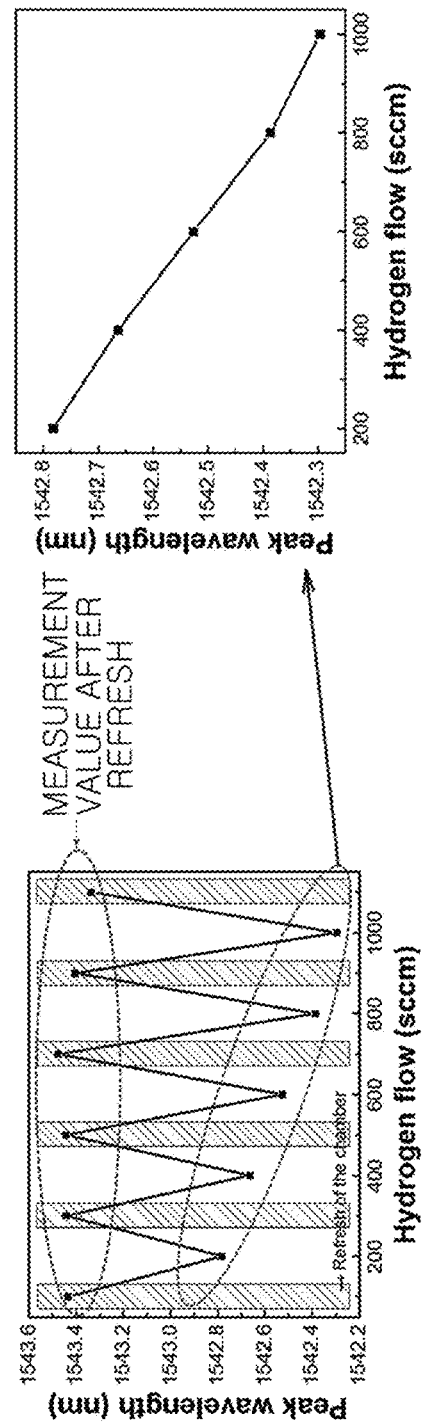
FIG. 8 is a graph showing the shift of a peak of the wavelength spectrum for each hydrogen concentration, according to an embodiment of the present disclosure.

FIG. 7 is a graph showing the shift of a wavelength spectrum according to a hydrogen concentration, according to an embodiment of the present disclosure, and FIG. 8 is a graph showing the shift of a peak of the wavelength spectrum for each hydrogen concentration, according to an embodiment of the present disclosure.

Referring to FIG. 7, the interference wave spectrum shifts according to the hydrogen concentration. The degree of shift of the interference wave spectrum increases according to the hydrogen concentration. The degree of shift of the interference wave spectrum is expressed as the shift of the peak of the interference wave spectrum.

Referring to FIG. 8, the wavelength of the peak of the interference wave spectrum is different for each concentration of hydrogen gas. The hydrogen gas detection system 200 detects the wavelength of the peak in the interference wave spectrum, and determines the concentration of hydrogen gas corresponding to the wavelength of the detected peak as the concentration of hydrogen gas detected by the sensor module 230. To this end, the hydrogen gas detection system 200 (e.g., the optical analyzer 240) may store in advance the relationship of wavelengths of the peaks for each hydrogen concentration.

For example, the optical analyzer 240 may also store the relationship of the wavelengths of the peaks for each hydrogen concentration expressed in the graph of FIG. 8. If so, when the wavelength of the peak is detected as 1542.3 nm, the system 200 may measure the current concentration of hydrogen gas as 1000 (sccm).

After the hydrogen gas is detected, if the detected hydrogen gas is removed to refresh the measurement environment, the shifted interference wave spectrum returns to its previous position before the shift.

If the change in the interference wave spectrum indicates a return to the previous position, the hydrogen gas detection system 200 may determine that the concentration of hydrogen gas is decreasing. Also, if the interference wave spectrum returns to the previous position after the change, the hydrogen gas detection system 200 may determine that the concentration of hydrogen gas is returned to the previous state.

The hydrogen gas detection system 200 may provide a user with the hydrogen gas analysis results, including the presence or absence of hydrogen gas, the concentration of hydrogen gas, and/or the change status of the hydrogen gas concentration. For example, the user may know that the leaked hydrogen gas is removed.

The hydrogen gas detection system 200 using the optical sensor does not require a power source or data communication material for the sensor node itself, so the system may be implemented in a simpler and more economical way, compared to a system using an electrical sensor.

In addition, the hydrogen gas detection system 200 may be operated to detect hydrogen gas through a plurality of sensor nodes located remotely from a single analysis instrument (e.g., OSA), so that it may have a wide and long-distance hydrogen detection range.

Figure 9:
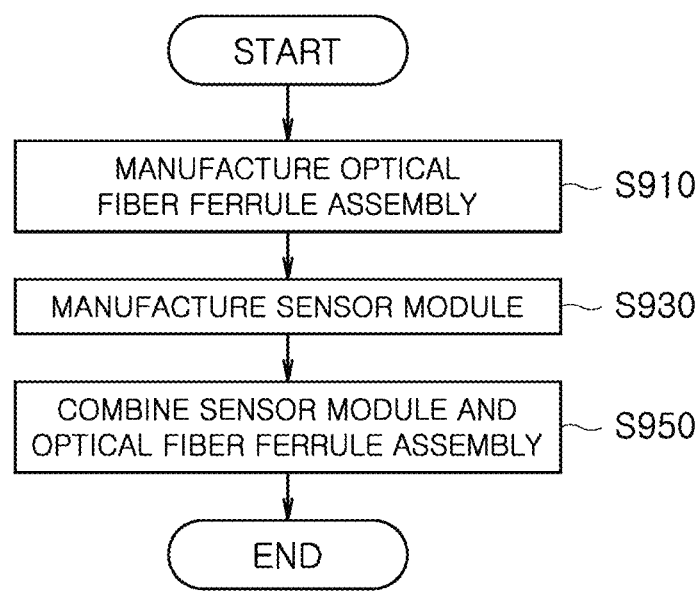
FIG. 9 is a flowchart for illustrating a process of manufacturing an optical sensor, according to an embodiment of the present disclosure.

FIG. 9 is a flowchart for illustrating a process of manufacturing an optical sensor, according to an embodiment of the present disclosure.

Referring to FIG. 9, the manufacturing process includes: manufacturing an optical fiber ferrule assembly (S910); manufacturing the sensor module 230 (S930); and combining the sensor module 230 and the optical fiber ferrule assembly (S950).

Figure 10:
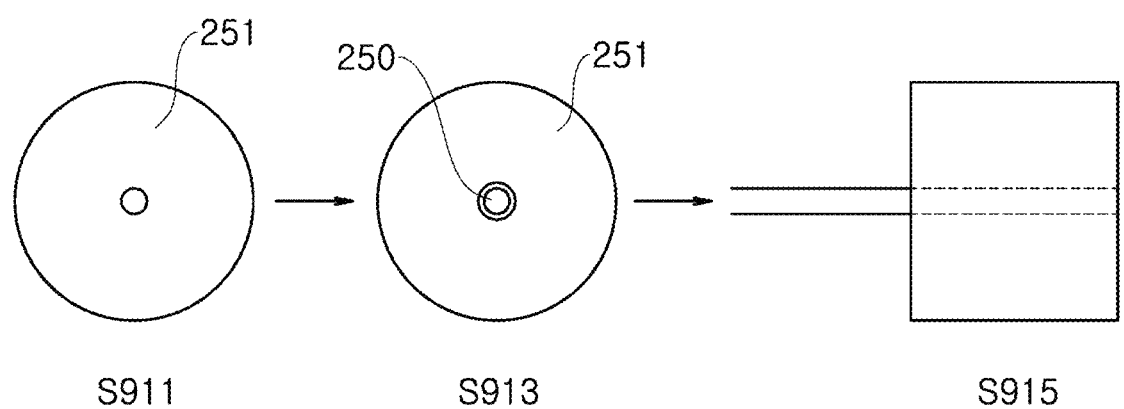
FIG. 10 is a diagram for illustrating a process of manufacturing the optical fiber ferrule of FIG. 9.

FIG. 10 is a diagram for illustrating a process of manufacturing the optical fiber ferrule of FIG. 9.

Referring to FIG. 10, the step (S910) includes: forming a path for the optical fiber 250 in one axial direction at the center of the ferrule 251 (S911); inserting and fixing the optical fiber 250 into the passage (S913); and polishing the surface of one side of the ferrule 251 together with the optical fiber 250 (S915).

In the step (S911), a perforated hole may be formed as a passage in the center of the ceramic ferrule 251.

The optical fiber 250 inserted in the step (S913) may be fixed by epoxy.

In the step (S915), the surface of one side of the ferrule 251 may be polished perpendicular to the direction in which the optical signal moves. Then, the surface of one side of the ferrule 251 serving as the first reflective surface is polished to face the surface of the support layer 233.

Figure 11:
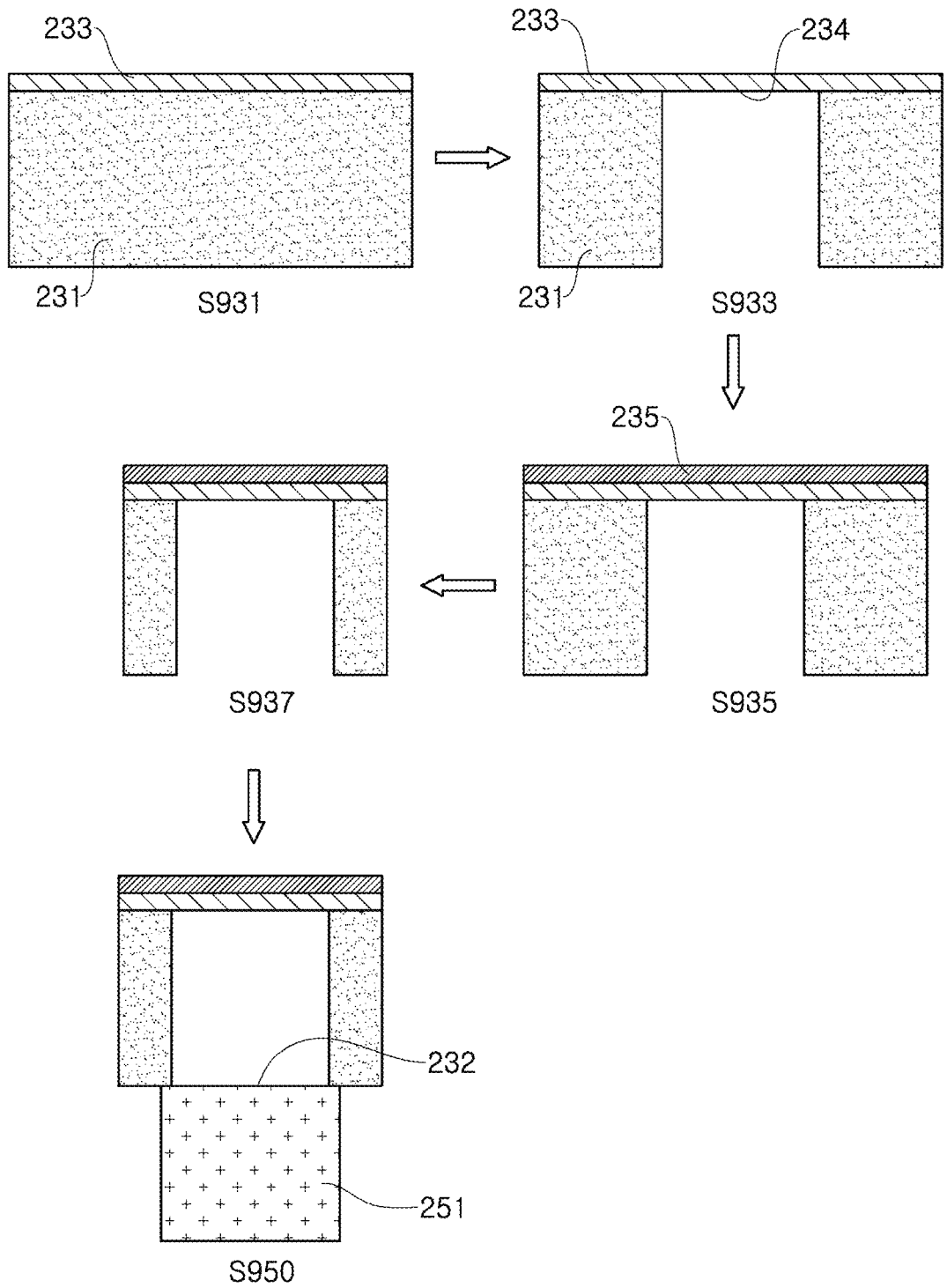
FIG. 11 is a diagram for illustrating a process of manufacturing the sensor module of FIG. 9.

FIG. 11 is a diagram for illustrating a process of manufacturing the sensor module of FIG. 9.

Referring to FIG. 11, the step (S930) includes: forming a support layer 233 on the silicon wafer (S931).

In an embodiment, the support layer 233 may be formed, for example, to have a thickness of 1 μm or less (S931). Since the support layer 233 is formed with a small thickness, the deformation of the hydrogen reaction layer 235 identically appears as the deformation of the support layer 233.

The step (S930) includes: etching and removing a portion of the silicon wafer (S933). The portion is a part for forming the cavity in the sensor module 230. A portion of the silicon wafer is etched so that one surface of the support layer 233 is exposed inside the perforated hole. As described above with reference to FIG. 3, the perforated hole is surrounded by a silicon wafer, so, if both sides of the perforated hole are blocked, etching is performed so that the inside of the perforated hole is not exposed to the outside.

The step (S930) includes: forming a hydrogen reaction layer 235 on the support layer 233 (S935).

The support layer 233 or the hydrogen reaction layer 235 is formed by various deposition techniques.

The step (S930) includes: cutting a non-etched layered portion in the stacked structure including the silicon wafer, the support layer 233 and the hydrogen reaction layer 235 (S937). In the step (S937), most portions of the stacked structure not in contact with the optical fiber ferrule assembly are cut to form the sensor module 230 (S937).

In the step (S950), the bottom surface of the sensor module 230 and one surface of the optical fiber ferrule assembly are arranged to contact each other.

In an embodiment, the holder 237 may be inserted into a structure in which the sensor module 230 and the optical fiber ferrule assembly are in contact (S950). In the step (S950), the holder 237 may be disposed to contact the sensor module 230 and the optical fiber ferrule assembly, thereby fixing the sensor module 230 and the optical fiber ferrule assembly.

Alternatively, the optical analyzer 240 may include a photodetector when the light source 210 is the laser diode. The photodetector is used to detect the spectrum of the interference wave in the laser light.

The optical analyzer 240 detects the change of the laser intensity originated from the transmittance change that is induced by the change of the spectrum periodicity of the interference wave. In this case, the hydrogen gas detection system 200 measures the change of the intensity of the constant wave induced by the shift of the interference spectrum. Then, the hydrogen gas detection system 200 senses the hydrogen gas and/or calculates the concentration of the hydrogen gas based on the change of the intensity of the constant wave.

A person with ordinary knowledge in the technical field to which the present disclosure belongs will be able to make various changes and modifications within a scope that does not deviate from the essential characteristics of the present disclosure. Therefore, the embodiments disclosed in the present disclosure are for explanation rather than limiting the technical idea of the present disclosure, and the scope of the technical idea of the present disclosure is not limited by these embodiments. The scope of protection of the present disclosure should be interpreted by the appended claims, and all technical ideas within the scope equivalent thereto should be interpreted as being included in the scope of the present disclosure.

REFERENCE SIGNS

200: hydrogen gas detection system
210: light source
220: circulator
230: sensor module
240: optical analyzer
250: optical fiber

The invention claimed is:

1. An optical sensor for sensing hydrogen gas, comprising:
   an optical fiber through which light moves;
   a ferrule formed at one end of the optical fiber to surround the optical fiber; and
   a sensor module configured to form an interference wave according to a Fabry-Perot interferometer with respect to light that moves through the optical fiber and is output from the optical fiber,
   wherein the sensor module includes a sensing material that expands and contracts by reacting with hydrogen gas, and
   wherein spectrum periodicity of the interference wave changes according to a volume change of the sensing material, and
   wherein the sensor module includes:
      a module case having a sidewall for forming a cavity so that one end of the sidewall is in contact with the ferrule;
      a support layer provided in contact with the other end of the sidewall; and
      a hydrogen reaction layer formed on the support layer and made of the sensing material.

2. The optical sensor according to claim 1,
   wherein the sensor module is attachable to and detachable from the ferrule, and
   wherein the light output from the optical fiber moves through the cavity between the ferrule and the support layer.

3. The optical sensor according to claim 1,
   wherein the interference wave is formed by repeated reflection and transmission of light between a first reflection surface formed at one end of the optical fiber where the light is output and a second reflection surface formed at a surface of the support layer in contact with the cavity, and
   wherein the spectrum periodicity of the interference wave changes as the support layer is deformed according to a volume change of the hydrogen reaction layer to change a distance between the second reflection surface and the first reflection surface.

4. The optical sensor according to claim 1, further comprising:
   a holder configured to fix a contact portion of the module case and the ferrule.

5. The optical sensor according to claim 1,
   wherein one end of the ferrule is inserted into a perforated hole of the module case so that the sensor module and the ferrule come into contact.

6. The optical sensor according to claim 1,
   wherein the sensing material includes palladium (Pd).

7. The optical sensor according to claim 1,
   wherein one ends of the ferrule and the optical fiber toward the cavity are polished perpendicular to the direction in which the light is output from the optical fiber.

8. A hydrogen gas detection system, comprising:
   at least one optical sensor according to claim 1;
   a light source configured to irradiate light to the optical fiber of the optical sensor; and
   an optical analyzer configured to detect whether hydrogen gas is present or to measure a concentration of the hydrogen gas based on the change of spectrum periodicity of the interference wave formed at the optical sensor.

9. The hydrogen gas detection system according to claim 8, further comprising:
   a circulator having first to third ports and configured to output the light formed at the light source and input to the first port to the sensor module connected to the second port, and to output the interference wave formed at the sensor module and input to the second port to the optical spectrum analyzer connected to the third port.

10. The hydrogen gas detection system according to claim 8,
    wherein the light source is a laser diode with a single operating wavelength,
    wherein the optical analyzer includes a photodetector to detect the change of the laser intensity that originated from the transmittance change induced by the change of the spectrum periodicity of the interference wave.

11. The optical sensor according to claim 1,
    wherein the sensor module is attachable to and detachable from the ferrule.

12. The optical sensor according to claim 1,
    wherein the light output from the optical fiber moves through the cavity between the ferrule and the support layer.

* * * * *